US00PP12202P2

(12) United States Plant Patent
Zary

(10) Patent No.: US PP12,202 P2
(45) Date of Patent: Nov. 13, 2001

(54) HYBRID TEA ROSE PLANT NAMED 'JACPINAP'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,222

(22) Filed: Dec. 6, 1999

(51) Int. Cl.[7] ..... A01H 5/00
(52) U.S. Cl. ..... Plt./130
(58) Field of Search ..... Plt./130, 132, 135, Plt./136

*Primary Examiner*—Howard J. Locker
(74) *Attorney, Agent, or Firm*—Klarquist Sparkman, LLP

(57) ABSTRACT

A hybrid tea rose plant having long stems bearing high centered fragrant flowers; dark green, glossy foliage; vigorous upright growth and resistance to mildew and rust.

1 Drawing Sheet

The present invention relates to a new and distinct variety of rose plant of the hybrid tea class which was originated by me by crossing an unnamed seedling, with the variety JACjubel (U.S. Plant Pat. No. 9,657).

The primary objective of this breeding was to produce a new rose variety having the long stems, high centered bud form and fragrance of the female parent combined with the dark, glossy foliage, excellent foliage health and vigor of the male parent. The objective was substantially achieved, along with other desirable improvements, as evidenced by the following unique combination of characteristics that are outstanding in the new variety and that distinguish it from its parents, as well as from all other varieties of which I am aware:

1. Glossy, dark green foliage;
2. Vigorous, upright growth;
3. Long cutting stems;
4. High centered flower form;
5. Fragrance; and
6. Novel flower color.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—Unnamed seedling (unnamed seedling× TANsenfrie (U.S. Plant Pat. No. 5,706)).

*Pollen parent.*—JACjubel (U.S. Plant Pat. No. 9,657).

Classification:

*Botanical.*—*Rosa hybrida.*

*Commercial.*—Hybrid tea.

FLOWER

Observations made from specimens grown in a garden environment at Somis, Calif. from March 1998 to August 1999.

Blooming habit: Continuous.

Bud:

*Size.*—1¾ inches long when the petals start to unfurl.

*Form.*—The bud form is long; pointed ovoid.

*Color.*—When sepals first divide, bud color is Orange-Red Group 31A except where the sepals have just unfolded. There it is Yellow Group 12C. When half blown, the upper sides of the petals are Orange-Red Group 31B on their outer ⅔'s. The inner ⅓'s are Yellow Group 12C, and the lower sides of the petals are Orange-Red Group 31C on their outer ⅔'s and Yellow Group 12C on the inner ⅓ of a petal.

*Sepals.*—Color: Green Group 138B. Surface texture: Covered in fine hairs. There are three normally appendaged sepals. There are two unappendaged sepals with hairy edges.

*Receptacle.*—Color: Yellow-Green Group 147A. Shape: Funnel. Size: Medium (about ¼ inch×3/16 inch). Surface: Smooth.

*Peduncle.*—Length: Short (about 2 to 2½ inches). Surface: Smooth; with a few glands. Color: Yellow-Green Group 147B. Strength: Stiff; erect.

Bloom:

*Size.*—Large. Average open size is 4½ inches.

*Borne.*—Singly.

*Stems.*—Strength: Strong. Average length is about 16 to 20 inches.

*Form.*—When first open: High centered. Permanence: Retains its form to the end; outer petals curl back.

*Petalage.*—Number of petals under normal conditions: 25 to 30.

*Color.*—The upper sides of the petals are Orange-Red Group 31B on their outer ⅔'s with the inner ⅓ of a petal Yellow Group 12C. The reverse sides of the petals are Orange-Red Group 31C on their outer ⅔'s, with Yellow Group 12C on the inner ⅓ of a petal. The base of each petal has a small ⅛ inch× ⅛ inch Yellow Group 13A half moon at the point of attachment on both surfaces. The major color on the upper side is Orange-Red Group 31B.

*Variegations.*—On the guard petals, along the midrib on the lower surface are occasional greenish-white streaks.

*Discoloration.*—The general tonality at the end of the first day: No change. At the end of the third day: No change. By day six, there is fading to Orange-Red Group 31D on the outer petal edges. This will extend to all petals by day seven or eight.

*Fragrance.*—Moderate; anise.

Petals:

*Texture.*—Thick.

*Shape.*—Round.

*Form.*—Tips slightly recurved.

*Arrangement.*—Imbricated. No petaloids in the center.

*Persistence.*—Petals drop off cleanly before drying.

*Lastingness.*—On the plant: Long (about seven to eight days). As a cut flower: Long (about eight to nine days).

Reproductive parts:

*Anthers.*—Size. Medium. Quantity: Many. Color: Yellow-Orange Group 22C. Arrangement: Regular around styles.

*Filaments.*—Color: Yellow-Group 13B.

*Pollen.*—Present.

*Styles.*—Color: Green-White Group 157A.

*Stigmas.*—Color: Greyed-Yellow Group 160B.

Plant:

*Form.*—Bush.

*Growth.*—Vigorous: upright; branching. At maturity, height is 5½ feet, width is 4½ feet.

Foliage: Number of leaflets on normal mid-stem leaves: five or seven.

*Size.*—Large (five inches long×3½ inches wide).

*Quantity.*—Abundant.

*Color.*—New foliage: Upper and lower surfaces: Greyed-Purple Group 183A. Old foliage: Upper surface: Green Group 139A. Lower surface: Green Group 139B.

Leaflets:

*Shape.*—Pointed oval.

*Texture.*—Leathery; glossy.

*Edge.*—Serrated.

*Serration.*—Single; small.

*Petiole rachis.*—Color: Upper side: Green Group 137B with some Greyed-Purple Group 185A on younger leaves. Lower side: Yellow-Green Group 148A.

*Petiole underside.*—Smooth; with occasional prickles.

*Stipules.*—Medium (about ¾ inch); serrated; bearded.

*Disease resistance.*—Resistant to mildew and rust, susceptible to blackspot under normal growing conditions.

Wood:

*New wood.*—Color: Greyed-Purple Group 183A. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium; straight.

*Color when young.*—Greyed-Purple Group 184B.

*Color when mature.*—Greyed-Orange Group 166A.

Small prickles:

*Quantity.*—On main stalks: None. On laterals: None.

I claim:

1. A new and distinct variety of rose plant of the hybrid tea class, substantially as herein shown and described, characterized particularly by having long stems bearing high centered fragrant flowers; dark green, glossy foliage; vigorous upright growth and resistance to mildew and rust.

* * * * *

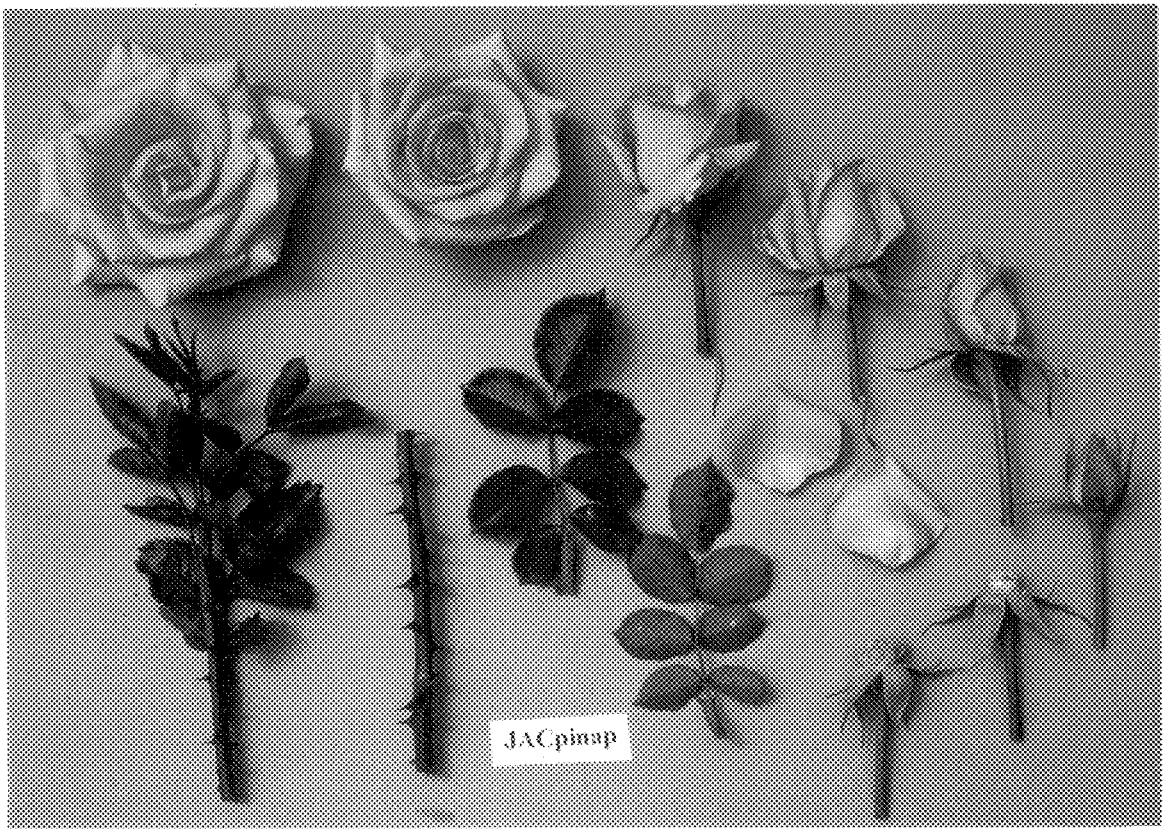
JACpinap